(12) United States Patent
Young et al.

(10) Patent No.: US 8,986,262 B2
(45) Date of Patent: Mar. 24, 2015

(54) SAMPLING CONNECTOR

(75) Inventors: Peter Jeffrey Young, King's Lynn (GB); Joseph Joachim Carter, King's Lynn (GB)

(73) Assignee: The Queen Elizabeth Hospital King's Lynn NHS Trust, King's Lynn (GB)

( * ) Notice: Subject to any disclaimer, the term of this patent is extended or adjusted under 35 U.S.C. 154(b) by 770 days.

(21) Appl. No.: 12/934,536

(22) PCT Filed: Mar. 25, 2009

(86) PCT No.: PCT/GB2009/000784
§ 371 (c)(1),
(2), (4) Date: Dec. 16, 2010

(87) PCT Pub. No.: WO2006/090148
PCT Pub. Date: Aug. 31, 2006

(65) Prior Publication Data
US 2011/0098598 A1 Apr. 28, 2011

(30) Foreign Application Priority Data

Mar. 25, 2008 (GB) .................................. 0805379.5

(51) Int. Cl.
*A61M 5/00* (2006.01)
*A61M 1/00* (2006.01)
(Continued)

(52) U.S. Cl.
CPC ........... *A61M 39/24* (2013.01); *A61M 39/1011* (2013.01); *A61M 2039/1077* (2013.01); *A61M 39/10* (2013.01); *A61M 39/223* (2013.01); *A61M 2039/0202* (2013.01);
(Continued)

(58) Field of Classification Search
CPC ............ A61M 39/10; A61M 39/1011; A61M 39/1077; A61M 39/1083; A61M 39/1088; A61M 39/2039
USPC ............ 600/575, 579; 604/32, 246–248, 320, 604/323, 533, 537, 538
See application file for complete search history.

(56) References Cited

U.S. PATENT DOCUMENTS

| 986,263 A | 3/1911 | Bevill |
|---|---|---|
| 4,219,021 A | 8/1980 | Fink |

(Continued)

FOREIGN PATENT DOCUMENTS

| EP | 0 495 419 A2 | 7/1992 |
|---|---|---|
| GB | 2 143 803 A | 2/1985 |
| WO | WO 2006/090148 A | 8/2006 |

*Primary Examiner* — Devin Henson
(74) *Attorney, Agent, or Firm* — Duane Morris LLP

(57) ABSTRACT

A sampling connector for use in sampling a body fluid such as arterial blood or cerebrospinal fluid. The sampling connector comprises at least two apertures in fluid communication via a fluid flow conduit and a one-way valve (14) disposed to allow fluid flow from the first aperture, through the fluid flow conduit and out of the second aperture, but not to allow fluid to flow into the second aperture and through the fluid flow conduit to the first aperture. In use, the sampling connector is connected to a body cavity to enable the sampling of a body fluid by withdrawal of the body fluid through the first aperture, and to prevent the introduction of a separate fluid to the body cavity. The first aperture can be within a male end and the second aperture can be within a female end or vice versa. A sampling device comprising a sampling connector according to the present invention and use of the sampling connector and/or sampling device is also claimed.

5 Claims, 2 Drawing Sheets

(51) Int. Cl.
  *A61B 5/00* (2006.01)
  *B65D 81/00* (2006.01)
  *A61M 39/24* (2006.01)
  *A61M 39/22* (2006.01)
  *A61M 39/10* (2006.01)
  *A61M 39/02* (2006.01)

(52) U.S. Cl.
  CPC . *A61M 2039/229* (2013.01); *A61M 2039/2473* (2013.01); *A61M 2039/2486* (2013.01); *A61M 2039/2493* (2013.01)
  USPC .......... 604/246; 604/247; 604/248; 604/323; 600/579

(56) References Cited

U.S. PATENT DOCUMENTS

| | | | |
|---|---|---|---|
| 4,307,731 A | | 12/1981 | Kaufman |
| 5,046,528 A | * | 9/1991 | Manska .................... 137/556 |
| 5,148,811 A | | 9/1992 | Messinger |
| 6,612,624 B1 | * | 9/2003 | Segal et al. ................. 285/330 |
| 2008/0067462 A1 | * | 3/2008 | Miller et al. .............. 251/149.1 |

* cited by examiner

SAMPLING CONNECTOR

The present invention relates to a sampling connector for use in sampling a body fluid.

In medical practice there are body cavities that require fluid sampling but into which the accidental injection of substances such as pharmaceutical products, glucose or even air is undesirable.

One example of such a body cavity is the arterial system. Blood samples are often withdrawn from the arterial system, most commonly from a three-way tap using a male luer syringe, to enable the measurement of blood gases, glucose and electrolytes. This sampling leads to the inherent risk of accidental intra-arterial injection potentially causing injury to the distal arterial tree.

In July 2008 the National Patient Safety Agency, part of the NHS, published a Rapid Response Report entitled "Problems with Infusions and Sampling from Arterial Lines". This report highlighted the fact that arterial lines are frequently used in medical practice to sample arterial blood but that serious harm to patients can result when poor sampling technique leads to a venous line being confused with an arterial line, and consequent injection of pharmaceutical products and/or glucose into an artery. Previous work in this area has tended to focus on the treatment of such complications but not on their prevention.

Another example of body cavities that require fluid sampling but into which the accidental injection of substances is undesirable is the subarachnoid space. Cerebrospinal fluid may be sampled from the subarachnoid space, most commonly from patients with external ventricular drains or lumbar drains to rule out the presence of infection. The complications of inadvertent injection into a subarachnoid space may be fatal or permanently disabling.

Additionally, a number of medical procedures require the one-way flow of body fluid, but the equipment normally used does not necessarily prevent the flow of body fluid in the "wrong direction". For example, cardiopulmonary bypass equipment requires blood to flow from the arterial system out of the body and back into the body via the venous system, however, user error can result in the reverse direction of fluid flow being enabled.

A novel solution to these problems is to place a one-way valve at a sampling port such that injection' cannot occur but sampling is unimpeded.

In accordance with one aspect of the present invention, there is provided a sampling connector for use in sampling a body fluid, which sampling connector comprises at least two apertures in fluid communication via a fluid flow conduit and a one-way valve disposed to allow fluid to flow from the first aperture, through the fluid flow conduit and out of the second aperture, but not to allow fluid to flow into the second aperture and through the fluid flow conduit to the first aperture, the arrangement being such that in use, the sampling connector is connected to a body cavity to enable the sampling of a body fluid by withdrawal of the body fluid through the first aperture and out of the second aperture, and to prevent the introduction of a separate fluid through the second aperture and the first aperture to the body cavity.

Hospitals use standardized medical equipment to enable ease of use and to increase efficiency. The sampling connector of the present invention will commonly comprise a male end comprising the first aperture because standard hospital practice connects a male end of a sampling connector to a body cavity to enable the withdrawal of a body fluid. Additionally, the sampling connector of the present invention will commonly comprise a female end comprising the second aperture because standard hospital practice connects a male syringe to a female end on a sampling connector to collect the withdrawn body fluid. However, the sampling connector of the present invention could operate in the reverse formation, with a female end comprising the first aperture and a male end comprising the second aperture, with a female syringe being used to collect the withdrawn body fluid from the male end.

A female end of the sampling connector may be in the form of a female luer connector that allows connection of a male luer connector, e.g. the male luer connector of a syringe, to enable blood sampling. Alternatively, a male end of the sampling connector may be in the form of a male luer connector that allows connection of a female luer connector, e.g. the female luer connector of a syringe, to enable blood sampling.

The sampling connector may be used as an "adaptor" for existing sampling devices so that once the sampling connector is connected to a sampling port of the sampling device, the sampling connector prevents injection into the sampling port. For example, a male end of the sampling connector may be connected to the female sampling port of the sampling device.

In one embodiment, the sampling connector includes a stop valve, such that when the sampling connector is connected to a body cavity, fluid cannot flow out of the second aperture of the sampling connector unless a complementary end of a separate device engages the second aperture of the sampling connector. The stop valve prevents body fluid spillage (e.g. blood spillage) from occurring when a separate device is not attached to the sampling connector. Preventing body fluid spillage is especially important when sampling from an, arterial line as, without a stop valve, the pumped flow of the arterial system can result in significant blood loss if the arterial sampling port is left open. The stop valve may form part of the one-way valve or may be separate from the one-way valve.

The stop valve may take the form of a luer slip reversible stop valve that opens to allow fluid flow only when a complementary luer slip connector is inserted. For example, the female end of the sampling connector may include a luer slip reversible stop valve that opens to allow fluid flow when a male luer slip connector is inserted.

In accordance with another aspect of the present invention, there is provided a sampling device comprising a sampling connector according to the present invention. Arterial blood sampling commonly uses an arterial cannula connected to a flush system comprising at least one sampling device. Usually the sampling device is a three-way tap, allowing the system to be flushed with saline or heparanised saline before and/or after blood sampling. The sampling device of the present invention may be a three-way tap.

In one embodiment the sampling connector is an integral part of the sampling device. For example, the sampling connector may be integrally formed within the sampling port of a three-way tap.

In another embodiment, the sampling connector may be used as an "adaptor" for existing sampling devices.

The sampling connector may be permanently connected to the sampling device, i.e. once the sampling connector is connected to the sampling device, the sampling connector is impossible to disconnect from the sampling device without causing damage to either the sampling device, the sampling connector or both such that re-connection is rendered impractical. The advantage of this is that once the device is connected a user (typically a clinician) is unable to accidentally disconnect the device. Mechanisms by which a permanent connection could be enabled include two very tightly tapered ends, and include a barbed male end that locks into place behind teeth on a female end. Specific examples of mechanisms enabling a permanent connection may be found in U.S. Pat. No. 4,323,065 and US 20060025751.

Alternatively, the sampling connector may be reversibly connected to the sampling device. Such a reversible connection may be provided by a luer lock connector or a luer slip connector, both of which are compatible with standardized medical equipment. The reversible connection between the sampling device and the sampling connector may be difficult to disconnect, wherein, in use, a user is impeded from removing the sampling connector. The advantage of a reversible connection that is difficult to disconnect is that once the sampling device and the sampling connector are connected a user is unlikely to accidentally disconnect the sampling connector from the sampling device. However, with considerable torque or force, disconnection may be possible if this is required. A reversible connection that is difficult to disconnect could result from a male end of the sampling connector being in the form of a luer lock or luer slip connector with an altered taper (for example the middle projection of the male end could have an altered taper) or altered dimensions so as to fit firmly or jam when connected to a female sampling port of a sampling device. A reversible connection that is difficult to disconnect could also result from the screw thread on the outer collar of a male end of the sampling connector becoming circumferentially narrower as the luer becomes further engaged with a female end on the sampling connector (or vice versa), or the pitch between the screw threads could reduce as a male end engages a female end. A specific example of a mechanism enabling a reversible connection that is difficult to disconnect may be found in US 20080172039.

The sampling connector and/or the sampling device may be color coded or include graphics (such as arrows or labeling) to indicate suitability for use in sampling a body fluid. The color coding and/or graphics may be desirable to indicate the function of the sampling connector and/or the sampling device, and to differentiate the sampling connector and/or the sampling device from other such devices. Standardized medical equipment uses the color red to indicate that a device is intended for use with an artery.

In order that the invention may be more fully understood the following non-limiting Examples are provided by way of illustration only and with reference to the accompanying drawings, in which.

Figure 1:
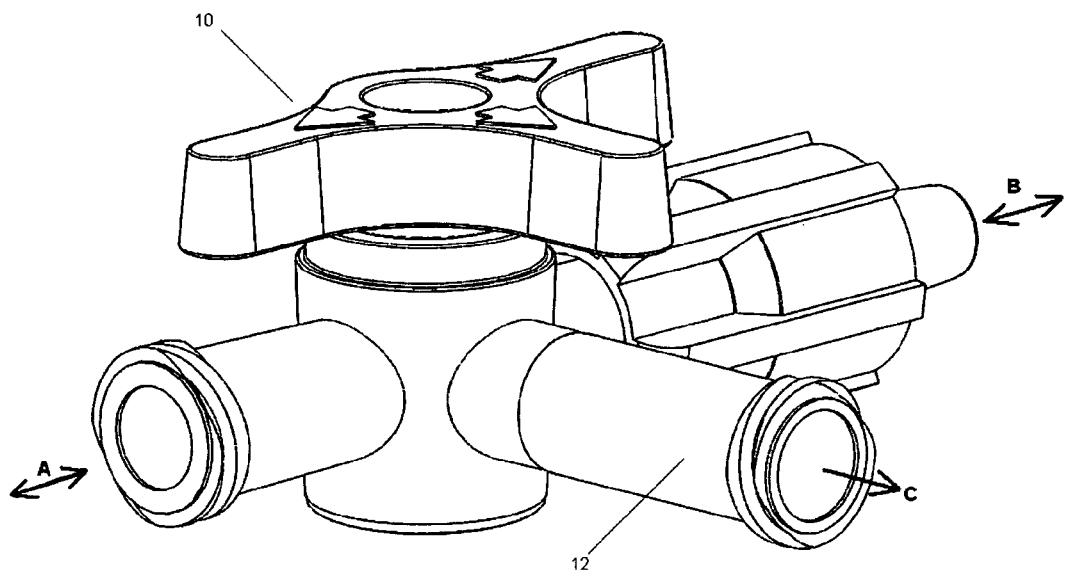
FIG. 1 depicts a first embodiment of a sampling device comprising a sampling connector according to the present invention.
Figure 2:
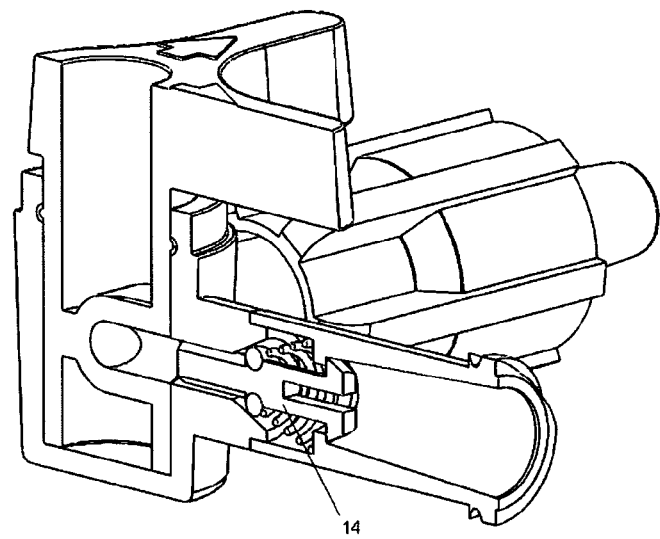
FIG. 2 is a section of a first embodiment of a sampling device comprising a sampling connector according to the present invention.

With reference to FIGS. 1 and 2, a sampling device 10 in the form of a three-way tap comprises a sampling port 12 that incorporates the claimed sampling connector. The sampling port 12 comprises a check valve 14. In use, a body fluid and/or a flushing solution can flow in the direction of arrows A and B through the sampling device 10, but the body fluid and/or a flushing solution can only flow out of the sampling port 12 in the direction of arrow C. This is because the check valve 14 prevents injection into the sampling device 10 through the sampling port 12. Additionally, should the tap of the sampling device 10 be left open, a body fluid cannot flow out of the device through sampling port 12 because the check valve 14 acts as a stop valve.

Figure 3:
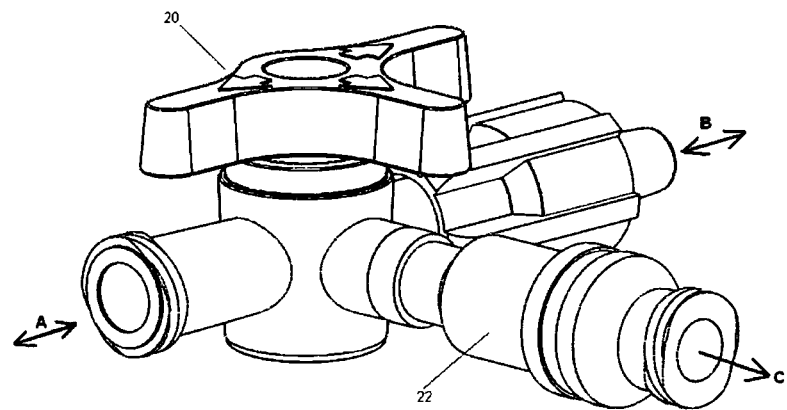
FIG. 3 depicts a second embodiment of a sampling device comprising a sampling connector according to the present invention.
Figure 4:
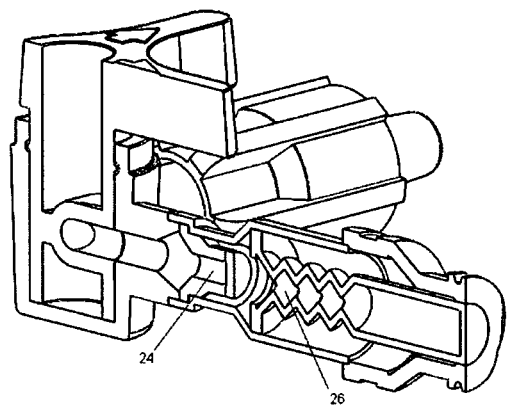
FIG. 4 is a section of a second embodiment of a sampling device comprising a sampling connector according to the present invention.

With reference to FIGS. 3 and 4, a sampling device 20 in the form of a three-way tap comprises a sampling port 22 that incorporates the claimed sampling connector. The sampling port 22 comprises a rubber valve 24 (also known as a flutter valve) and a stop valve 26. In use, a body fluid and/or a flushing solution can flow in the direction of arrows A and B through the sampling device 20, but the body fluid and/or a flushing solution can only flow out of the sampling port 22 in the direction of arrow C. This is because the rubber valve 24 prevents injection into the sampling device 20 through the sampling port 22. Additionally, should the tap of the sampling device 20 be left open, a body fluid cannot flow out of the device through sampling port 22 because of the stop valve 26.

EXAMPLE 1

Conventional Arterial Blood Sampling

Method of Sample Collection:
- Remove the bung from the sampling port integrated into the transducer element and swab the port clean;
- Attach a 5 ml syringe to the sampling port and rotate a three-way tap located within the arterial line system to allow blood to flow from the patient up the arterial line system to the transducer element;
- Aspirate on the 5 ml syringe until blood just reaches the transducer element;
- Remove the bung from the sampling port integrated into the three-way tap and swab the port clean;
- Attach a 2 ml syringe to the sampling port and rotate the three-way tap to close off the connection to the transducer element and open the sampling port integrated into the three-way tap;
- Aspirate a small amount of blood (approx. 0.5 ml) on the 2 ml syringe to remove any heparanised saline present in the three-way tap mechanism;
- Remove the 2 ml syringe and attach an arterial blood gas syringe and collect blood sample from the patient; and
- Close the three-way tap and remove sample.

Method of Flushing the Line:
- Squeeze the one-way valve at the transducer to allow the pressurized heparanised saline to flush the line;
- Rotate the three-way tap to close off the connection to the patient and open the sampling port integrated into the three-way tap;
- Place a piece of gauze around the sampling port and squeeze the one-way valve at the transducer to allow the pressurized heparanised saline to flush the sampling port; and
- Attach clean bungs to the sampling port and the transducer port after removal of the 5 ml syringe from the sampling port integrated into the transducer element.

EXAMPLE 2

Arterial Blood Sampling Using the Claimed Sampling Connector

Method of Sample Collection:
- Remove the bung from the sampling port integrated into the transducer element and swab the port clean;
- Attach a 5 ml syringe to the sampling port and rotate a three-way tap located within the arterial line system to allow blood to flow from the patient up the arterial line system to the transducer element;

Aspirate on the 5 ml syringe until blood just reaches the transducer element;

Swab the sampling port integrated into the three-way tap clean (which sampling port incorporates the claimed sampling connector);

Attach a 2 ml syringe to the sampling port (incorporating the claimed sampling connector);

Aspirate a small amount of blood (approx. 0.5 ml) on the 2 ml syringe to remove any heparanised saline present in the three-way tap mechanism;

Remove the 2 ml syringe and attach an arterial blood gas syringe and collect blood sample from the patient; and Remove sample.

Method of Flushing the Line:

Squeeze the one-way valve at the transducer to allow the pressurized heparanised saline to flush the line;

Attach a second 2 ml syringe to the sampling port (incorporating the claimed sampling connector) and squeeze the one-way valve at the transducer to allow the pressurized heparanised saline to flush the sampling port and fill the 2 ml syringe;

Remove and discard the 2 ml syringe; and

Attach a clean bung to the sampling port integrated into the transducer element after removal of the 5 ml syringe.

The method described in Example 2 clearly involves fewer rotations of the three-way tap than the method described in Example 1. Alternative arrangements for arterial blood sampling can use two three-way taps, one to switch between a flow of flushing solution and a flow of blood and a second to provide a sampling port for blood sample collection. In arrangements using two three-way taps, the three-way tap used for blood sample collection can include the claimed sampling connector with a stop valve at its sampling port. When such an arrangement is used for arterial blood sampling only the three-way tap that switches between a flow of flushing solution and a flow of blood need be rotated and the three-way tap used for blood sample collection can be left "open" and need not be adjusted.

The fact that the use of the claimed sampling connector involves fewer rotations of three-way taps demonstrates that not only does the sampling connector prevent injection into a body cavity into which the accidental injection of substances is undesirable, but also that use of the sampling connector improves the fluid sampling process. This suggests that once sampling connectors are made available commercially, that user compliance is likely to be high.

The invention claimed is:

1. A sampling connector for use as an adaptor for a three-way tap arterial blood sampling device, which sampling connector comprises at least two apertures in fluid communication via a fluid flow conduit and a one-way valve disposed to allow fluid to flow from a first aperture, through the fluid flow conduit and out of a second aperture, but not to allow fluid to flow into the second aperture and through the fluid flow conduit to the first aperture, characterized in that the first aperture is within a male end and the second aperture is within a female end and said male end of the sampling connector is a luer lock connector with an altered taper or altered dimensions so as to fit firmly or jam when connected to a female sampling port of the sampling device, such that the sampling connector is reversibly connectable to the sampling device and is difficult to disconnect from the sampling device by fitting firmly or jamming when connected to a sampling port of a sampling device, and such that the one-way valve is configured to prevent the introduction of a separate fluid through the second aperture and the first aperture to a body cavity, wherein in use a user is impeded from removing the sampling connector.

2. The sampling connector according to claim 1, wherein the sampling connector additionally comprises a stop valve, such that when the sampling connector is connected to a body cavity, fluid cannot ROW out of the second aperture of the sampling connector unless a complementary end of a separate device engages the second aperture of the sampling connector.

3. The sampling connector according to claim 1, wherein the sampling connector is color coded to indicate suitability for use in sampling a body fluid.

4. The sampling device according to claim 3, wherein the sampling device is a three-way tap.

5. A sampling g device comprising a sampling connector for use as an adaptor for a three-way tap arterial blood sampling device, which sampling connector comprises at least two apertures in fluid communication via a fluid flow conduit and a one-way valve disposed to allow fluid to flow from a first aperture, through the fluid flow conduit and out of a second aperture, but not to allow fluid to flow into the second aperture and through the fluid flow conduit to the first aperture, characterized in that the first aperture is within a male end and the second aperture is within a female end and said male end of the sampling connector is a luer lock connector with an altered taper or altered dimensions so as to fit firmly or jam when connected to a female sampling port of the sampling device, such that the sampling connector is reversibly connectable to sampling device and is difficult to disconnect from the sampling device by fitting firmly or jamming when connected to a sampling port of a sampling device, and such that the one-way valve is configured to prevent the introduction of a separate fluid through the second aperture and the first aperture to a body cavity, wherein in use a user is impeded from removing the sampling connector.

* * * * *